(12) United States Patent
Tanigawara et al.

(10) Patent No.: US 9,459,254 B2
(45) Date of Patent: Oct. 4, 2016

(54) METHOD FOR DETERMINING SENSITIVITY TO AN ANTICANCER AGENT

(75) Inventors: Yusuke Tanigawara, Tokyo (JP); Sayo Suzuki, Tokyo (JP); Hidehiro Irie, Tokyo (JP); Akito Nishimuta, Tokyo (JP); Tetsuya Suzuki, Tokyo (JP); Shinji Sugimoto, Tokyo (JP)

(73) Assignees: KEIO UNIVERSITY, Tokyo (JP); KABUSHIKI KAISHA YAKULT HONSHA, Tokyo (JP)

( * ) Notice: Subject to any disclaimer, the term of this patent is extended or adjusted under 35 U.S.C. 154(b) by 645 days.

(21) Appl. No.: 13/505,143

(22) PCT Filed: Oct. 29, 2010

(86) PCT No.: PCT/JP2010/069362
§ 371 (c)(1),
(2), (4) Date: Apr. 30, 2012

(87) PCT Pub. No.: WO2011/052748
PCT Pub. Date: May 5, 2011

(65) Prior Publication Data
US 2012/0220613 A1 Aug. 30, 2012

(30) Foreign Application Priority Data

Oct. 30, 2009 (JP) .................................. 2009-250257
Feb. 1, 2010 (JP) .................................. 2010-020456

(51) Int. Cl.
*G01N 33/53* (2006.01)
*G01N 33/574* (2006.01)
*A61K 31/4745* (2006.01)
*A61K 31/513* (2006.01)
*A61K 45/06* (2006.01)

(52) U.S. Cl.
CPC ......... *G01N 33/574* (2013.01); *A61K 31/4745* (2013.01); *A61K 31/513* (2013.01); *A61K 45/06* (2013.01); *G01N 2800/52* (2013.01)

(58) Field of Classification Search
None
See application file for complete search history.

(56) References Cited

U.S. PATENT DOCUMENTS

2009/0162839 A1* 6/2009 Katz et al. ................. 435/6
2010/0323034 A1 12/2010 Tanigawara et al.

FOREIGN PATENT DOCUMENTS

| CA | 2 541 903 A1 | 10/2007 |
|---|---|---|
| CA | 2 713 296 A1 | 8/2009 |
| CN | 1588045 A | 3/2005 |
| WO | WO 2007/002069 A2 | 1/2007 |
| WO | WO 2007/071914 A1 | 6/2007 |
| WO | 2009 096189 | 8/2009 |
| WO | 2009 096196 | 8/2009 |

OTHER PUBLICATIONS

Bons et al (Respiratory Medicine, 2007, 101: 1687-1695).*
Koomen et al (Clinical Cancer Research, 2005, 11: 1110-1118).*
Kusama et al (Breast Cancer Res Treat, 2004, 88(1): Abstract).*
Liotta (Gynecologic Oncology, 2003, 88: S25-S28).*
Petricoin et al (Lancet, 2002, 359: 572-577).*
Vlahou et al (Journal of Biomedicine and Biotechnology, 2003, 308-314).*
Wiseman et al (Drugs, 1996, 52(4): Abstract).*
Pusztai et al (Cancer, 2004, 100(9): 1814-1822).*
U.S. Appl. No. 13/504,985, filed Apr. 30, 2012, Tanigawara, et al.
U.S. Appl. No. 13/505,175, filed Apr. 30, 2012, Tanigawara, et al.
U.S. Appl. No. 14/007,145, filed Sep. 24, 2013, Tanigawara, et al.
Extended European Search Report Issued Mar. 12, 2013 in Patent Application No. 10826878.0.
Eun-Kyoung Yim et al., "Proteomic Analysis of Antiproliferative Effects by Treatment of 5-Fluorouracil in Cervical Cancer Cells", DNA and Cell Biology, XP055055064, vol. 23, No. 11, 2004, pp. 769-776.
Lajos Pusztai et al., "Pharmacoproteomic Analysis of Prechemotherapy and Postchemotherapy Plasma Samples from Patients Receiving Neoadjuvant or Adjuvant Chemotherapy for Breast Carcinoma", Cancer, XP055055068, vol. 100, No. 9, May 1, 2004, pp. 1814-1822.
Takagi, K., et al., "CDK Inhibitor enhances the sensitivity to 5-FU in colorectal cancer cells," 66th Annual Meeting of the Japan Cancer Association Koen Yoshishu, p. 45, (Aug. 25, 2007).
Shimada, Y., et al., "Phase II Study of CPT-11, a New Camptothecin Derivative, in Metastatic Colorectral Cancer," Journal of Clinical Oncology, vol. 11, No. 5, pp. 909-913, (May 1993).
Cunningham, D., et al., "A Phase III Study of Irinotecan (CPT-11) Versus Best Supportive Care in Patients with Metastatic Colorectal Cancer Who Have Failed 5-Fluorouracil Therapy," Seminars in Oncology, vol. 26, No. 1, pp. 6-12, (Feb. 1999).
Rougier, P., et al,. "Randomised trial of irinotecan versus fluorouracil by continuous infusion after fluorouracil failure in patients with metastatic colorectal cancer," The Lancet, vol. 352, pp. 1407-1412, (Oct. 31, 1998).

(Continued)

*Primary Examiner* — Sean Aeder
(74) *Attorney, Agent, or Firm* — Oblon, McClelland, Maier & Neustadt, L.L.P

(57) ABSTRACT

To provide a marker for determining sensitivity of a patient to an anti-cancer agent, and novel cancer therapeutic means employing the marker.

The marker for determining sensitivity to an anti-cancer agent is formed of a protein selected from the group consisting of a protein or a fragment thereof which is detected as a peak at m/z of 16,450 to 16,620, a protein or a fragment thereof which is detected as a peak at m/z of 22,080 to 22,310, and a protein or a fragment thereof which is detected as a peak at m/z of 17,100 to 17,270, the peaks being determined by means of a mass spectrometer.

22 Claims, 4 Drawing Sheets

(56) References Cited

OTHER PUBLICATIONS

Pitot, H.C., et al., "N9841: A randomized phase III equivalence trial of irinotecan (CPT-11) versus oxaliplatin/5-fluorouracil (5FU)/ leucovorin (FOLFOX4) in patients (pts) with advanced colorectal cancer (CRC) previously treated with 5FU," Journal of Clinical Oncology, 2005 ASCO Annual Meeting Proceedings, vol. 23, No. 16S, Abstract #3506, Total 4 Pages, (Jun. 1, 2005).

Saltz, L.B., et al., "Irinotecan Plus Fluorouracil and Leucovorin for Metastatic Colorectal Cancer," New England Journal of Medicine, vol. 343, No. 13, pp. 905-914, (2000).

Douillard, J.Y., et al., "Irinotecan combined with fluorouracil compared with fluorouracil alone as first-line treatment for metastatic colorectal cancer: a multicentre randomised trial," The Lancet, vol. 355, pp. 1041-1047, (Mar. 25, 2000).

Kawato, Y., et al., "Intracellular Roles of SN-38, a Metabolit of the Camptothecin Deivative CPT-11, in the Antitumor Effect of CPT-11," Cancer Research, vol. 51, pp. 4187-4191, (Aug. 15, 1991).

Cecchin, E., et al., "Carboxylesterase Isoform 2 mRNA Expression in Peripheral Blood Mononuclear Cells Is a Predictive Marker of the Irinotecan to SN38 Activation Step in Colorectal Cancer Patients," Clinical Cancer Research, vol. 11, No. 19, pp. 6901-6907, (Oct. 1, 2005).

Tanimoto, K., et al., "Human carboxylesterase 1A2 expressed from carboxylesterase 1A1 and 1A2 genes is a potent predictor of CPT-11 cytotoxicity in vitro," Pharmacognetics and Genomics, vol. 17, pp. 1-10, (2007).

Potti, A., et al., "Genomic signatures to guide the use of chemotherapeutics," Nature Medicine, vol. 12, No. 11, pp. 1294-1300, (Nov. 2006).

Sorensen, N.M., et al., "TIMP-1 Is Significantly Associated with Objective Response and Surivival in Metastatic Colorectal Cancer Patients Receiving Combination of Irinotecan, F-Fluorouracil, and Folinic Acid," Clinical Cancer Research, vol. 13, No. 14, pp. 4117-4122, (Jul. 15, 2007).

Van Kuilenburg, A.B.P., "Dihydropyrimidine dehydrogenase and the efficacy and toxicity of 5-fluorouracil," European Journal of Cancer, vol. 40, pp. 939-950, (2004).

Aschele, C., et al., "Thymidylate Synthase expression as a predictor of clinical response to fluoropyrimidine-based chemotherapy in advanced colorectal cancer," Cancer Treatment Reviews, vol. 28, pp. 27-47, (2002).

Popat,S., et al., " Thymidylate Synthase Expression and Prognosis in Colorectal Cancer: A Systematic Review and Meta-Analysis," Journal of Clinical Oncology, vol. 22, No. 3, pp. 529-536, (Feb. 1, 2004).

Paradiso, A., et al., "Topoisomerase-I, Thymidylate Synthase Primary Tumour Expression and Clinical Efficacy of 5-FU/CPT-11 Chemotherapy in Advanced Colorectal Cancer Patients," International Journal of Cancer, vol. 111, pp. 252-258, (2004).

International Search Report Issued Nov. 30, 2010 in PCT/JP10/69362 Filed Oct. 29, 2010.

Combined Chinese Office Action and Search Report issued Nov. 28, 2013 in Patent Application No. 201080049197.8 (with partial English language translation).

* cited by examiner

METHOD FOR DETERMINING SENSITIVITY TO AN ANTICANCER AGENT

TECHNICAL FIELD

The present invention relates to a marker for use in determination of the sensitivity of a cancer patient to an anti-cancer agent to be administered thereto, which marker can determine whether or not the cancer of the patient has a therapeutic response to the anti-cancer agent, and to application of the marker.

BACKGROUND ART

Anti-cancer agents have various types such as an alkylating agent, a platinum agent, an antimetabolite, an antitumor antibiotic, and an antitumor plant alkaloid. These anti-cancer agents are effective for some cancers but not effective for other cancers. Even when an anti-cancer agent is confirmed to be effective for a certain cancer, the anti-cancer agent is effective for some patients and not effective for other patients, leading to interindividual differences. Whether or not a cancer of a specific patient has response to an anti-cancer agent is designated as sensitivity to the anti-cancer agent.

Irinotecan hydrochloride (CPT-11) is an anti-cancer agent which has been developed in Japan and which has a mechanism of antitumor action based on the inhibition of topoisomerase I. In Japan, CPT-11 indicated for non-small-cell lung cancer, small cell lung cancer, cervical cancer, and ovarian cancer was approved as an effective drug in January, 1994. Further, CPT-11 indicated for gastric cancer, colorectal cancer, breast cancer, squamous cell carcinoma, and malignant lymphoma was approved in July, 1995. Currently, CPT-11 in multi-drug therapy has been recognized to be one of standard chemotherapy, in particular, as a first-line or a second-line for colorectal cancer all over the world, and CPT-11 had been established the efficacy (Non-Patent Documents 1 to 6).

Meanwhile, clinical performance (including survival rate) attained by chemotherapy for advanced or metastatic colorectal cancer has been drastically improved through a combination therapy employing a key drug such as CPT-11 or oxaliplatin, which launched in 1990s, and a fluoro-pyrimidine drug such as fluorouracil (5-FU), which had been a main drug for the colorectal cancer therapy. However, the response rate of such chemotherapy is as low as about 50%. That is, the chemotherapy is not effective for half of the patients to whom an anti-cancer agent has been administered, concomitant with risky severe adverse events. Thus, there is urgent demand for establishing a marker for predicting the sensitivity to an anti-cancer agent, which marker enables determination of interindividual therapeutic response (i.e., responder/non-responder).

Although CPT-11 itself has anti-tumor activity, CPT-11 is activated by carboxyl esterase in the body, to thereby be converted into 7-ethyl-10-hydroxycamptothecin (SN-38), which has an anti-tumor activity about 100 times to some thousand times that of CPT-11. Co-presence of CPT-11 and SN-38 is thought to provide an anti-tumor effect. In hepatocytes, SN-38 is glucuronidated by UDP-glucuronosyltransferase (UGT), to thereby form SN-38 glucuronate conjugate (SN-38G) having no cytotoxicity. SN-38G is excreted mainly to bile and then transferred to the intestinal tract, and finally excreted to feces. A portion of SN-38G excreted to the intestinal tract is deconjugated by β-glucuronidase of enteric bacteria, to thereby form active SN-38 again. The thus-formed free SN-38 is metabolized and excreted via the steps of re-absorption by the mediation of a transporter present at the intestinal tract epithelium, enterohepatic circulation, glucuronate conjugation by UGT in intestinal epithelial cells, and the like (Non-Patent Document 7). In the course of this metabolism, SN-38 damages the intestinal mucosa, to thereby possibly induce diarrhea. Also, some studies revealed that SN-38 adversely affects bone marrow, where cell division actively occurs, to thereby induce erythrocytopenia, leukocytopenia, and thrombocytopenia.

One cause for adverse events such as severe diarrhea and neutropenia was confirmed to be a change in exposure amount of SN-38 in the body caused by genetic polymorphism of UGT1A1. However, regarding therapeutic effects, there has not been reported that the therapeutic effect can be predicted by pharmacokinetics, due to the complex disposition, which include conversion of CPT-11 (pro-drug) to SN-38 (active metabolite) and its detoxication; re-generation of SN-38 in the course of enterohepatic circulation; and metabolism of CPT-11 and formation of SN-38 from the metabolite thereof, and due to antitumor effect generally determined by the tumor-related factors. Meanwhile, it has been reported that the carboxyl esterase mRNA expression amount in peripheral mononuclear cells correlates with the AUC ratio of SN-38 to SN-38G but does not correlate with the tumor reduction effect (Non-Patent Document 8).

There have also been reported the following tumor-related factors relating to the sensitivity or resistance to CPT-11: mutation of topoisomerase I, which is a target of SN-38, and expression amount thereof; activity of carboxyl esterase, the enzyme being involved in transformation of CPT-11 to SN-38 (Non-Patent Document 9); and transporters (multi-drug resistance protein (MRP)-1, MRP-2, and breast cancer resistant protein (BCRP)/ABCG2), which affect the intracellular accumulation of CPT-11 and SN-38. Studies have also been conducted on correlations of cell proliferation antigen Ki-67, tumor suppressor gene p53, etc. with response to CPT-11 therapy. Quite recently, in vitro, studies have been conducted to predict sensitivity to an anticancer agent systematically through combination of anti-cancer agent sensitivity data with microarray analysis data, and for camptothecin derivatives, topotecan has been studied (Non-Patent Document 10). Also, a clinical study have revealed that the plasma TIMP-1 level, TIMP-1 being a tissue inhibitor of metalloproteinase-1 having anti-apoptosis action, is significantly correlated with the clinical prognosis of a metastatic colorectal cancer patient having undergone CPT-11+5-FU combination therapy (Non-Patent Document 11).

In FOLFIRI regimen, which is a key regimen for colorectal cancer therapy, CPT-11 and 5-FU are administered in combination. 5-FU is a fluoro-pyrimidine anti-cancer agent which was developed in 1957. Even now, 5-FU is a basic chemotherapy drug for gastrointestinal cancer. When incorporated into cancer cells, 5-FU exerts cytotoxic effect through a principle action mechanism of DNA synthesis inhibition induced by inhibition of thymidylate synthase (TS) by an active metabolite, fluorodeoxyuridine-5'-monophosphate (FdUMP), and another mechanism of RNA function inhibition by an active metabolite, 5-fluorouridine triphosphate (FUTP).

Hitherto, many studies have been conducted to predict therapeutic response to fluoro-pyrimidine anti-cancer agents. In particular, many studies have been focused on dihydropyrimidine dehydrogenase (DPD), which is a 5-FU degrading enzyme, and thymidylate synthase (TS), which is a target enzyme of an active metabolite. A tumor in which DPD, a rate-limiting enzyme in the catabolism of 5-FU, is highly expressed is reported to have resistance to 5-FU (Non-Patent Document 12), but a limited number of studies have been conducted with clinical specimens. The TS expression level is reported to be a possible factor that determines the therapeutic effect by a fluoro-pyrimidine anti-cancer agent, even when the expression level is determined through any assay method such as the enzymatic activity method, protein level assay, or RNA level assay (Non-Patent Documents 13 and 14).

However, the above-obtained results are not completely the same, and there has been known no definite biomarker which can predict the therapeutic response to 5-FU in an early treatment stage.

As described above, many studies have been conducted on sensitivity (to 5-FU, CPT-11, and 5-FU/CPT-11) predicting bio-markers due to their necessity. However, a study has revealed that neither topoisomerase I (target) nor TS (possible 5-FU-sensitivity predictive factor) has clear correlation with therapeutic response in 5-FU/CPT-11 combination therapy (Non-Patent Document 15). Therefore, no definite bio-marker capable of predicting therapeutic response has been established.

Furthermore, since the therapy schedule of cancer chemotherapy generally requires a long period of time, continuous monitoring of sensitivity of a target patient to a target anti-cancer agent during the therapy can determine whether or not the therapy should be continued. Thus, such monitoring is thought to be meritorious from the viewpoints of reduction or mitigation of the burden on patients and adverse events, leading to reduction in medical cost. Therefore, there is keen demand for establishment of a biomarker that can predict the effect of 5-FU, CPT-11, or a combination of 5-FU/CPT-11 or that can determine therapeutic response in an early stage, for the purpose of predicting therapeutic response of individual patients and establishing diagnosis in an early stage to select an appropriate drug and treatment regimen; i.e., for realizing "personalized therapy."

PRIOR ART DOCUMENTS

Non-Patent Documents

Non-patent Document 1: J. Clin. Oncol. 1993; 11: 909-913
Non-patent Document 2: Semin. Oncol. 1999; 26 (1 Suppl. 5): 6-12
Non-patent Document 3: Lancet 1998; 352: 1407-1412
Non-patent Document 4: Pro. ASCO 2005; Abstract #3506
Non-patent Document 5: N. Engl. J. Med. 2000; 343: 905-914
Non-patent Document 6: Lancet 2000; 355: 1041-1047
Non-patent Document 7: Cancer Res. 1991; 51: 4187-4191
Non-patent Document 8: Clin. Cancer Res. 2005; 11: 6901-6907
Non-patent Document 9: Pharmacogenet Genomics 2007; 17: 1-10
Non-patent Document 10: Nat. Med. 2006; 12: 1294-1300
Non-patent Document 11: Clin. Cancer Res. 2007; 13: 4117-4122
Non-patent Document 12: European Journal of Cancer 2004; 40: 939-950
Non-patent Document 13: Cancer Treatment Reviews 2002; 28: 27-47
Non-patent Document 14: J. Clin. Oncol. 2004; 22: 529-536
Non-patent Document 15: Int. J. Cancer 2004; 111: 252-258

SUMMARY OF THE INVENTION

Problems to be Solved by the Invention

An object of the present invention is to provide a marker for determining sensitivity of a patient to an anti-cancer agent, which marker can determine whether or not the patient has a therapeutic response to the anti-cancer agent. Another object is to provide novel cancer therapeutic means employing the marker.

Means for Solving the Problems

In order to attain the aforementioned objects, the present inventors have searched for a marker for determining sensitivity to an anti-cancer agent by culturing human cancer cells, exposing the cells to a drug, and comprehensively analyzing the time-dependent expression profiles of intracellular proteins after exposure to the drug by means of a surface-enhanced laser desorption/ionization time-of-flight mass spectrometer (SELDI-TOF MS). More specifically, two types of human colorectal cancer cells, one having high sensitivity to 5-FU, SN-38 (active metabolite of CPT-11), and combination of 5-FU/SN-38 and the other having low sensitivity thereto, were exposed to 5-FU (single drug), SN-38 (single drug), or 5-FU/SN-38 (combination), and the time-dependent expression profiles of intracellular proteins after exposure to the drug were investigated. As a result, the inventors have found, after exposure to 5-FU, a protein exhibiting an increase in intracellular expression level in high-sensitivity cells. The protein or a fragment thereof has been detected as a peak at m/z, as determined by means of a mass spectrometer, of 16,450 to 16,620.

Similarly, the inventors have found, after exposure to SN-38, proteins exhibiting an increase in intracellular expression level in high-sensitivity cells. The proteins or fragments thereof have been detected as a peak at m/z, as determined by means of a mass spectrometer, of 16,450 to 16,620 or 22,080 to 22,310.

Furthermore, the inventors have found, after exposure to 5-FU/SN-38 in combination, a protein exhibiting an increase in intracellular expression level in high-sensitivity cells. The protein or a fragment thereof has been detected as a peak at m/z, as determined by means of a mass spectrometer, of 16,450 to 16,620. The inventors have also found a protein exhibiting an increase in intracellular expression level in low-sensitivity cells. The protein or a fragment thereof has been detected as a peak at m/z, as determined by means of a mass spectrometer, of 17,100 to 17,270.

Separately, the inventors have found, before exposure to any of these drugs, several proteins exhibiting intracellular expression levels which differ between high-sensitivity cells and low-sensitivity cells. These proteins or fragments thereof have been detected as a peak at m/z, as determined by means of a mass spectrometer, of 16,450 to 16,620, 17,100 to 17,270, or 22,080 to 22,310.

On the basis of these findings, the inventors have carried out further studies, and have found that whether or not a cancer of a target cancer patient has a sensitivity to 5-FU therapy, SN-38 therapy, or 5-FU/SN-38 combination therapy can be determined through measuring the relevant protein level of a biological sample derived from the cancer patient; that screening of an anti-cancer agent sensitivity enhancer can be accomplished through employment of variation in expression of the substance as an index; and that the therapeutic effect of the relevant anti-cancer agent can be drastically enhanced by use, in combination, of the anticancer agent sensitivity enhancer and the anti-cancer agent which is a sensitivity enhancement target of the enhancer. The present invention has been accomplished on the basis of these findings.

Accordingly, the present invention provides a marker for determining sensitivity to an anti-cancer agent, the marker comprising a protein selected from the group consisting of a protein or a fragment thereof which is detected as a peak at m/z of 16,450 to 16,620 (hereinafter referred to as protein A), a protein or a fragment thereof which is detected as a peak at m/z of 22,080 to 22,310 (hereinafter referred to as protein B), and a protein or a fragment thereof which is detected as a peak at m/z of 17,100 to 17,270 (hereinafter referred to as protein C), the peaks being determined by means of a mass spectrometer.

The present invention also provides a method for determining sensitivity of a subject to an anti-cancer agent, the method comprising measuring the level of any of proteins A, B, and C in a specimen derived from the subject.

The present invention also provides a kit for carrying out the method for determining sensitivity of a subject to an anti-cancer agent, the kit comprising a protocol for measuring the level of any of proteins A, B, and C in a specimen derived from the subject.

The present invention also provides a screening method for an anti-cancer agent sensitivity enhancer, the method comprising employing variation in expression of any of the proteins A, B, and C as an index.

The present invention also provides an anti-cancer agent sensitivity enhancer obtained through the screening method.

The present invention also provides a composition for cancer therapy comprising, in combination, the anti-cancer agent sensitivity enhancer and an anti-cancer agent which is a sensitivity enhancement target of the enhancer.

The present invention also provides the proteins A, B, and C for use in determining the anti-cancer agent sensitivity.

Effects of the Invention

According to the marker for determining sensitivity to an anti-cancer agent of the present invention, the sensitivity to an anti-cancer agent of a patient can be appropriately determined before the therapy or in an early stage after start of the therapy. As a result, an anti-cancer agent having higher therapeutic effect can be selected, and unnecessary adverse events, which would otherwise result from administration of an anti-cancer agent exerting no expected therapeutic effect, can be prevented. Meanwhile, the therapy schedule employing an anti-cancer agent generally requires a long period of time. Even in on-going therapy, the sensitivity of the target cancer to an anti-cancer agent can be evaluated in a time-dependent manner through determination of the anti-cancer agent sensitivity in each therapy cycle, whereby a determination can be made on whether or not the therapy should be continued. As a result, progression of cancer and aggravation of adverse events, which would otherwise result from continuous administration of an anti-cancer agent exerting no expected therapeutic effect, can be prevented. Thus, reductions can be expected in the burden on patients and medical cost.

In addition, when the marker of the present invention is used, a drug which can promote anti-cancer agent sensitivity can be selected through screening. Thus, through employment, in combination, of the target anti-cancer agent and an anti-cancer agent sensitivity enhancer to the anti-cancer agent, the expected cancer therapeutic effect can be drastically enhanced. The assay reagent for measuring the marker for determining sensitivity to an anti-cancer agent of the present invention is useful as an reagent for determining sensitivity to an anti-cancer agent.

MODES FOR CARRYING OUT THE INVENTION

Figure 1:
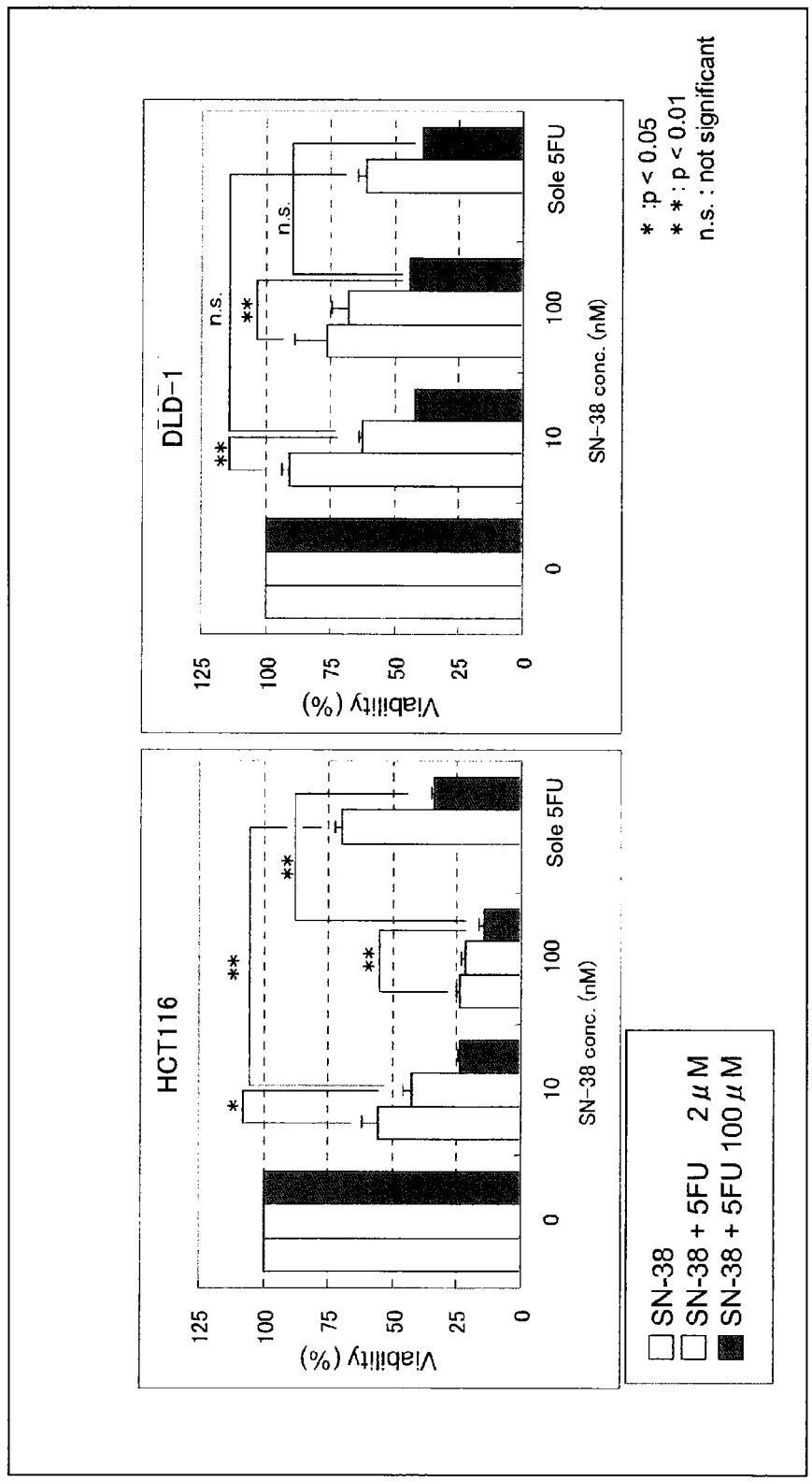
FIG. 1 A graph showing the survival (%) of HCT116 cells under exposure (72 hours) to 5-FU, SN-38, or 5-FU/SN-38, and a graph showing the survival (%) of DLD-1 cells under exposure (72 hours) to 5-FU, SN-38, or 5-FU/SN-38.

The marker for determining sensitivity to an anti-cancer agent of the present invention is any of proteins A to C. More specifically, the proteins are detected by means of a cation-exchange chip at a pH of 4.5, and m/z peaks are determined by means of a surface-enhanced laser desorption/ionization time-of-flight mass spectrometer (SELDI-TOF MS). Thus, the proteins are a protein or a fragment thereof which is detected as a peak at m/z of 16,450 to 16,620, (hereinafter referred to as protein A), a protein or a fragment thereof which is detected as a peak at m/z of 22,080 to 22,310 (hereinafter referred to as protein B), and a protein or a fragment thereof which is detected as a peak at m/z of 17,100 to 17,270 (hereinafter referred to as protein C), the peaks being determined by means of a mass spectrometer.

As shown in the Examples described hereinbelow, through investigation of intracellular protein expression in cultured cancer cells by means of a SELDI-TOF MS, protein A level was found to increase in HCT116 cells, which are high-sensitive to any of 5-FU, SN-38, and 5-FU/SN-38 combination, after exposure to 5-FU, SN-38, or 5-FU/SN-38 combination. In contrast, no significant difference was observed in DLD-1 cells, which are low-sensitive to any of 5-FU, SN-38, and 5-FU/SN-38 combination. Therefore, protein A is useful as markers for determining sensitivity to an anti-cancer agent, particularly as markers for determining sensitivity to 5-FU, SN-38, or 5-FU/SN-38.

As shown in the Examples described hereinbelow, through investigation of intracellular protein expression in cultured cancer cells by means of a SELDI-TOF MS, protein B level was found to increase in HCT116 cells, which are high-sensitive to SN-38, after exposure to SN-38. In contrast, no significant difference was observed in DLD-1 cells, which are low-sensitive to SN-38, or protein B level tended to decrease. Therefore, protein B is useful as a marker for determining sensitivity to an anti-cancer agent, particularly as a marker for determining sensitivity to SN-38.

As shown in the Examples described hereinbelow, through investigation of intracellular protein expression in cultured cancer cells by means of a SELDI-TOF MS, protein C level was found to increase in DLD-1 cells, which are low-sensitive to 5-FU/SN-38 combination, after exposure to 5-FU/SN-38 combination. In contrast, no significant difference was observed in HCT116 cells, which are high-sensitive to 5-FU/SN-38 combination. Therefore, protein C is useful as a marker for determining sensitivity to an anti-cancer agent, particularly as a marker for determining sensitivity to 5-FU/SN-38 combination.

As shown in the Examples described hereinbelow, intracellular levels of proteins A to C in HCT116 cells, which are high-sensitive to 5-FU, SN-38, and 5-FU/SN-38 combination, before exposure to any of the drugs (not exposed) were significantly higher than those in DLD-1 cells, which are low-sensitive to the aforementioned drugs. Therefore, proteins A to C are useful as markers for determining sensitivity to an anti-cancer agent, particularly as markers for determining sensitivity to 5-FU, SN-38, or 5-FU/SN-38 combination.

No particular limitation is imposed on the anti-cancer agent to which the marker for determining sensitivity to an anti-cancer agent of the present invention is applied. Examples of the anti-cancer agent include oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab/ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof. Among them, fluoro-pyrimidine anti-cancer agents and plant alkaloid-derived anti-cancer agents are preferred, with fluorouracil, irinotecan, SN-38, and salts thereof being particularly preferred. The marker of the present invention is preferably applied to a combination of fluorouracil or a salt thereof with irinotecan, SN-38, or a salt thereof.

In order to determine sensitivity of a subject to an anti-cancer agent by use of the marker for determining sensitivity to an anti-cancer agent of the present invention, the level of any of the protein A to protein N level in a specimen may be measured. Examples of the specimen include biological samples derived from subjects having cancer (i.e., cancer patients) such as blood, serum, plasma, cancer tissue biopsy specimens, cancer isolated preparations, feces, urine, ascitic fluid, pleural fluid, cerebrospinal fluid, and expectoration. Of these, serum is particularly preferred.

Examples of the target cancer of the present invention include lip, oral, pharyngeal cancers such as pharyngeal cancer; gastrointestinal cancers such as esophageal cancer, gastric cancer, and colorectal cancer; respiratory and intrathoracic organ cancers such as lung cancer; bone cancer and articular cartilage cancer; skin melanoma, squamous cell cancer, and other skin cancers; mesothelial and soft tissue cancers such as mesothelioma; female genital cancers such as breast cancer, uterine cancer, and ovarian cancer; male genital cancers such as prostate cancer; urinary tract cancers such as bladder cancer; eye, brain, and central nervous system cancers such as brain tumor; thyroid and other endocrine cancers; lymphoid tissue, hematopoietic tissue, and related tissue cancers such as non-Hodgkin's lymphoma and lymphoid leukemia; and metastatic cancers from these cancers as primary lesions. The present invention is particularly preferably applied to gastric cancer and colorectal cancer.

Proteins A to C contained in a specimen may be measured through, for example, SELDI-TOF MS or immunoassay.

Measurement through SELDI-TOF MS may be performed through the procedure as described in the Examples. In the immunoassay techniques, an immunoassay employing anti-protein A antibody to anti-protein C antibody are preferably employed. The employed anti-protein A antibody to anti-protein C antibody may be a monoclonal or polyclonal antibody. Specific examples of the immunoassay include radioimmunoassay, enzyme immunoassay, fluorescent immunoassay, luminescent immunoassay, immunoprecipitation, immunonephelometry, Western blotting, immunostaining, and immunodiffusion. Among them, Western blotting and enzyme immunoassay are preferably employed. Western blotting and enzyme-linked immunosorbent assay (ELISA) (e.g., sandwich ELISA) are particularly preferred.

In the case where proteins A and B are employed with respect to a target anti-cancer agent, the sensitivity of the target cancer to the anti-cancer agent is determined as follows. The level of any of the proteins A and B in a biological sample derived from a cancer patient is measured before and after administration of the anti-cancer agent. When the protein A level or protein B level tends to increase after administration of the anti-cancer agent, the cancer is determined to have sensitivity to the anti-cancer agent, whereas when the protein A level or protein B level is constant or decreases after administration of the anti-cancer agent, the cancer is determined to have no sensitivity to the anti-cancer agent. Specifically, when the level of any of proteins A and B is higher than a predetermined standard level in an early stage after administration of the anti-cancer agent, the cancer can be determined to have sensitivity to the anti-cancer agent. Thus, the proteins may be employed as a marker for indicating that the patient is expected to receive therapeutic effect and may positively undergo continuous therapy employing the anti-cancer agent.

When the level of any of proteins A and B is lower than a predetermined standard level in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to avoid progression of cancer and aggravation of adverse events which would otherwise be caused by continuous administration of an ineffective anti-cancer agent.

In the case where protein C is employed and 5-FU/SN-38 combination is a target anti-cancer agent, the sensitivity of the target cancer to the anti-cancer agent is determined as follows. The level of protein C in a biological sample derived from a cancer patient is measured before and after administration of the anti-cancer agent. When the protein C level tends to increase after administration of the anti-cancer agent, the cancer is determined to have no sensitivity to the anti-cancer agent, whereas when the protein C level is constant or decreases after administration of the anti-cancer agent, the cancer is determined to have sensitivity to the anti-cancer agent. Specifically, when the protein C level is lower than a predetermined standard level in an early stage after administration of the anti-cancer agent, the cancer can be determined to have sensitivity to the anti-cancer agent. Thus, the protein may be employed as a marker for indicating that the patient is expected to receive therapeutic effect and may positively undergo continuous therapy employing the anti-cancer agent.

When the protein C level is higher than a predetermined standard level in an early stage after administration of the anti-cancer agent, the cancer can be determined to have no sensitivity to the anti-cancer agent. When the cancer has no sensitivity to the anti-cancer agent, no pharmaceutical effect can be expected from the anti-cancer agent. If such an ineffective anti-cancer agent is continuously administered to the patient, the cancer may progress, and adverse events may be aggravated. Thus, the marker for determining sensitivity to an anti-cancer agent of the present invention may be employed not only to determine therapeutic response to the anti-cancer agent, but also to avoid progression of cancer and aggravation of adverse events which would otherwise be caused by continuous administration of an ineffective anti-cancer agent.

In the case where proteins A to C are employed and any of 5-FU, SN-38, and 5-FU/SN-38 combination is a target anti-cancer agent, the sensitivity of the target cancer to the anti-cancer agent is determined as follows. The level of any of the proteins in a biological sample derived from a cancer patient is measured before administration of the anti-cancer agent. When the level of any of these proteins is lower than a predetermined standard level, the cancer can be determined to have no sensitivity to the anti-cancer agent. In the case where the cancer has no sensitivity to the target anti-cancer agent, conceivably, no pharmaceutical effect is expected, and merely adverse events caused by the anti-cancer agent occur. Thus, the the marker for determining sensitivity to an anti-cancer agent of the present invention may be employed to avoid occurrence of unnecessary adverse events as well as to avoid progression of cancer and aggravation of adverse events which would otherwise be caused by continuation of ineffective therapy.

In contrast, when the level of any of these proteins is higher than a predetermined standard level, the cancer can be determined to have sensitivity to the anti-cancer agent. Thus, the proteins may also be employed as a marker for positively selecting a patient who is expected to receive therapeutic effect.

When protein C is employed as a marker for use during administration of the anti-cancer agent, in the case where the protein level is constant or decreases after administration, the cancer can be determined to have sensitivity to the anti-cancer agent, whereas when protein C is employed as a marker for use before administration of the anti-cancer agent, in the case where the protein level is lower than a predetermined level, the cancer can be determined to have no sensitivity to the anti-cancer agent. Since the marker plays different roles between during administration of the anti-cancer agent and before administration thereof, the marker is preferably employed in consideration of the difference.

In order to carry out the method of the present invention for determining sensitivity of a subject to an anti-cancer agent, preferably, a kit containing a protocol for measuring the level of proteins A to C of a specimen is employed. The kit contains a reagent for measuring any of proteins A to C, an indication of an instruction manual for use of the reagent, standards for determining the presence or absence of sensitivity to the anti-cancer agent, etc. The standards include standard levels of proteins A to C, a high threshold level, a low threshold level, factors affecting the measurements, the degree of the effects, etc. These levels may be set so as to suit the target anti-cancer agent selected. The sensitivity determination may be performed as described above on the basis of the standards.

In the case where proteins A and B are employed, screening of an anti-cancer agent sensitivity enhancer can be performed through employment of variation in expression of any of the proteins, specifically elevation of the expression. That is, a substance which elevates expression of protein A or B in vitro or in vivo enhances sensitivity to an anti-cancer agent. For example, a substance which elevates protein A level and protein B level in various cancer cells in the presence of an anti-cancer agent (in vitro) is a substance which enhances the sensitivity to the anti-cancer agent (i.e., anti-cancer agent sensitivity enhancer). Also, a substance which promotes elevation of protein levels in a cancer-bearing animal after administration of an anti-cancer agent (in vivo) is a substance which enhances the sensitivity to the anti-cancer agent (i.e., anti-cancer agent sensitivity enhancer).

In the case where protein C is employed and 5-FU/SN-38 combination is a target anti-cancer agent, screening of an anti-cancer agent sensitivity enhancer can be performed through employment of variation in expression of protein C, specifically suppression of the expression. That is, a substance which suppresses expression of protein C in vitro or in vivo enhances sensitivity to an anti-cancer agent. For example, a substance which lowers protein C level in various cancer cells in the presence of an anti-cancer agent (in vitro) is a substance which enhances the sensitivity to the anti-cancer agent (i.e., anti-cancer agent sensitivity enhancer). Also, a substance which promotes lowering of protein level C in a cancer-bearing animal after administration of an anti-cancer agent (in vivo) is a substance which enhances the sensitivity to the anti-cancer agent (i.e., anti-cancer agent sensitivity enhancer).

In the case where proteins A to C are employed and any of 5-FU, SN-38, and 5-FU/SN-38 combination is a target anti-cancer agent, screening of an anti-cancer agent sensitivity enhancer can be performed through employment of variation in expression of any of the proteins, specifically elevation of the expression. That is, a substance which elevates expression of protein in vitro or in vivo enhances sensitivity to an anti-cancer agent. For example, a substance which elevates protein levels in various cancer cells in the absence of an anti-cancer agent (in vitro) is a substance which enhances the sensitivity to the anti-cancer agent (i.e., anti-cancer agent sensitivity enhancer). Also, a substance which promotes elevation of protein levels in a cancer-bearing animal before administration of an anti-cancer agent (in vivo) is a substance which enhances the sensitivity to the anti-cancer agent (i.e., anti-cancer agent sensitivity enhancer). Notably, since the behavior of protein C differs between the case of exposure to the anti-cancer agent and that of non-exposure thereto, screening of the anti-cancer agent sensitivity enhancer is preferably performed in consideration of the difference.

Through employment, in combination, of the thus-obtained anti-cancer agent sensitivity enhancer and an anti-cancer agent which is a sensitivity enhancement target of the enhancer, the therapeutic effect of the anti-cancer agent is drastically enhanced. The combination of the anti-cancer agent sensitivity enhancer and the anti-cancer agent which is a sensitivity enhancement target of the enhancer may be a composition containing both ingredients, or a combined drug of preparations containing individual ingredients. These two ingredients may be administered through different routes.

The target anti-cancer agents which may be employed here are the same as described above. Examples of the anti-cancer agent include oxaliplatin, cyclophosphamide, ifosfamide, thiotepa, melphalan, busulfan, nimustine, ranimustine, dacarbazine, procarbazine, temozolomide, cisplatin, carboplatin, nedaplatin, methotrexate, pemetrexed, fluorouracil, tegaful/uracil, doxifluridine, tegaful/gimeracil/oteracil, capecitabine, cytarabine, enocitabine, gemcitabine, 6-mercaptopurine, fuludarabin, pentostatin, cladribine, hydroxyurea, doxorubicin, epirubicin, daunorubicin, idarubicine, pirarubicin, mitoxantrone, amurubicin, actinomycin D, bleomycine, pepleomycin, mytomycin C, aclarubicin, zinostatin, vincristine, vindesine, vinblastine, vinorelbine, paclitaxel, docetaxel, irinotecan, irinotecan active metabolite (SN-38), nogitecan (topotecan), etoposide, prednisolone, dexamethasone, tamoxifen, toremifene, medroxyprogesterone, anastrozole, exemestane, letrozole, rituximab, imatinib, gefitinib, gemtuzumab/ozogamicin, bortezomib, erlotinib, cetuximab, bevacizumab, sunitinib, sorafenib, dasatinib, panitumumab, asparaginase, tretinoin, arsenic trioxide, salts thereof, and active metabolites thereof. Among them, fluoropyrimidine anti-cancer agents and plant alkaloid-derived anti-cancer agents are preferred, with fluorouracil, irinotecan, SN-38, and salts thereof being particularly preferred. It is preferably applied to a combination of fluorouracil or a salt thereof with irinotecan, SN-38, or a salt thereof.

EXAMPLES

The present invention will next be described in more detail by way of examples.

Example 1

(1) Method (a) Cells Employed

Two human colorectal cancer cell lines (HCT116 and DLD-1) were obtained from ECACC. Cell culturing was performed by means of a φ100 mm/Tissue Culture Dish (IWAKI) with a medium (D-MEM, 2 mM glutamine, 10% fetal bovine serum) at 37° C. under 5% $CO_2$.

(b) Drugs

Fluorouracil (5-FU) was purchased from Sigma, and SN-38 powder was obtained from Kabushiki Kaisha Yakult Honsha.

(c) Evaluation of Sensitivity of Cancer to SN-38, 5-FU, and a Combination of 5-FU and SN-38 (5-FU/SN-38)

Two colorectal cancer lines (HCT116 and DLD-1, obtained from ECACC) were exposed to a drug, and 48 hours and 72 hours after drug exposure, cell viability was determined by means of an MTS assay (CellTiter96™ $AQ_{ueous}$ One Solution Cell Proliferation Assay, Promega). Drug exposure conditions were as follows. 5-FU (single agent) was used at the following 11 concentrations: control (0 μM), 0.001 μM, 0.01 μM, 0.1 μM, 1 μM, 3 μM, 10 μM, 30 μM, 100 μM, 1,000 μM, and 10,000 μM. SN-38 (single agent) was used at the following 11 concentrations; control (0 nM), 0.001 nM, 0.01 nM, 0.1 nM, 0.3 nM, 1 nM, 3 nM, 10 nM, 30 nM, 100 nM, and 1,000 nM. In the case of 5-FU/SN-38 combination, 5-FU was used at 2 μM, 10 μM, 30 μM, and 100 μM (4 concentrations), and SN-38 was used at 0.001 nM, 0.01 nM, 0.1 nM, 0.3 nM, 1 nM, 3 nM, 10 nM, 30 nM, 100 nM, and 1,000 nM (10 concentrations); i.e., 40 concentrations were employed. In addition, the above four 5-FU (single agent) concentrations, which were the same as employed in the case of 5-FU/SN-38 combination, and control (0 μM) were employed. Sensitivity evaluation was performed by use of three samples with respect to each cell line, drug exposure time, and drug exposure concentration in one experiment. The experiment was performed thrice by use of cells at different passage numbers.

Sensitivity analysis was performed from viability data calculated from MTS assay results. The presence or absence of combined effect was determined through comparison of viability obtained by exposure to a combination with that obtained by exposure to a single agent at the same concentration as employed at the exposure to the combination. When the viability obtained by exposure to a combination is significantly lowered as compared with each single agent case, the presence of a combination effect was confirmed.

(d) Drug Exposure Test

Based on the results of (c) above, the drug concentration employed in the exposure test was determined. The 5-FU+SN-38 combination concentration was adjusted to the following four levels: 2 μM+10 nM, 2 μM+100 nM, 100 μM+10 nM, and 100 μM+100 nM, the 5-FU concentration (exposure to single agent) was adjusted to 2 μM and 100 μM, and the SN-38 concentration (exposure to single agent) was adjusted to 10 nM and 100 nM. In addition, the exposure test was conducted at a drug-free concentration (control). That is, nine concentrations in total were employed. Drug exposure time was adjusted to the following four periods of time: 0 hour (just before exposure), 4 hours, 24 hours, and 48 hours. After completion of exposure, cell count was performed, and intracellular proteins were extracted.

(e) Extraction of Intracellular Proteins

The medium was removed from the dish and washed thrice with ice-cooled PBS. The cells on the dish was collected by scraping with a rubber policeman. The thus-obtained cell suspension was transferred to a 1.5-mL microtube. The cell suspension was centrifuged at 4° C. and 1,200×g for 10 minutes, and the cells were recovered. After removal of the supernatant, a cell lysis buffer (9 mol/L urea, 2% CHAPS, 1 mM DTT, protease-inhibitor cocktail (Sigma)) was added in a volume of 200 μL with respect to 10,000,000 cells. The liquid was subjected to untrasonic treatment under cooling with ice. The thus-treated product was centrifuged at 4° C. and 16,000×g for 20 minutes, and the supernatant was quickly frozen with liquid nitrogen. The frozen product was stored at −80° C. before analysis. An aliquot of the supernatant was subjected to protein quantification (DC Protein Assay Kit, Bio-Rad).

(f) Preparation of Samples for Protein Expression Analysis with ProteinChip, and Expression Analysis of Intracellular Proteins The protein sample was mixed with a cell lysis buffer (excluding protease inhibitor), to thereby adjust the protein concentration to 2.5 mg/mL. The liquid was further mixed with a dilution/washing buffer (pH: 4.5, 50 mM sodium acetate buffer) (hereinafter referred to simply as "buffer"), to a protein concentration of 0.5 mg/mL. The thus-prepared sample (100 μL) was applied to spots of a cation-exchange ProteinChip array (CM10, Bio-Rad) which had been conditioned in advance with the same buffer. Incubation was performed for one hour for reaction, and the chip array was washed thrice with the buffer and rinsed twice with milliQ water, followed by drying in air. Energy absorbing molecule (EAM: saturated solution of sinapinic acid in 50% ACN/ 0.5% TFA) (1.0 µL (0.5 mL×2)) was added to each spot. After the surface of the spot was dried, analysis of the ProteinChip array was performed.

Protein expression analysis was performed through surface-enhanced laser desorption/ionization time-of-flight mass spectrometry (SELDI-TOF MS). As an analyzer, ProteinChip™ Reader (Model PCS4000 Personal Edition, Bio-Rad) was used and the analysis was performed under the following conditions: mass range of 0 to 70,000 Da, focus mass of 8,000 Da, energy of 4,000 nJ, and 265 shots/sample.

Peak extraction (signal-to-noise ratio (S/N)≥2) and protein expression comparative analysis were performed by means of CiphergenExpress™ Data Manager 3.0.

(g) Selection of Candidate Peaks

Through SELDI-TOF MS analysis, 112 to 147 protein peaks were selected from each sample (S/N≥2). Firstly, a peak cluster was made by means of CiphergenExpress™ Data Manager 3.0. Then, under tested conditions, there were selected peaks exhibiting a significant change in intensity over time after exposure to a drug, and peaks exhibiting significantly different intensities depending on the selected drug at exposure times (4, 24, and 48 hours). Then, peaks overlapping the above two conditions; i.e., peaks exhibiting variation in expression due to exposure time and depending on the type of the drug, were selected.

(2) Results (a) Evaluation of Drug Sensitivity of HCT116 and DLD-1

The cell viabilities after exposure to 100 µM 5-FU for 48 hours were about 24% (HCT116) and about 49% (DLD-1). Thus, DLD-1 was found to have sensitivity to 5-FU lower than that of HCT116. The cell viabilities after exposure to 100 nM SN-38 for 72 hours were about 24% (HCT116) and about 76% (DLD-1). Thus, DLD-1 was found to have sensitivity to SN-38 lower than that of HCT116. Regarding 5-FU/SN-38 combination, HCT116 exhibited significantly lower cell viabilities after exposure to 2 µM 5-FU+10 nM SN-38 and 100 µM 5-FU+100 nM SN-38 for 72 hours, as compared with the cases where corresponding single agents were used, indicating a combination effect. However, DLD-1 exhibited no significant combination effect. Therefore, HCT116 was found to have high sensitivity to 5-FU/SN-38 combination, and DLD-1 was found to have low sensitivity to 5-FU/SN-38 combination (FIG. 1).

(b) Protein Expression Analysis

Through proteome analysis employing SELDI-TOF MS, variation in intracellular protein level associated with exposure to 5-FU, SN-38, or 5-FU/SN-38 combination was comprehensively analyzed. The analysis was performed through a technique as described in (1) above. As a result, the following proteins exhibiting characteristic level variations after exposure to the drugs were selected.

Figure 2:
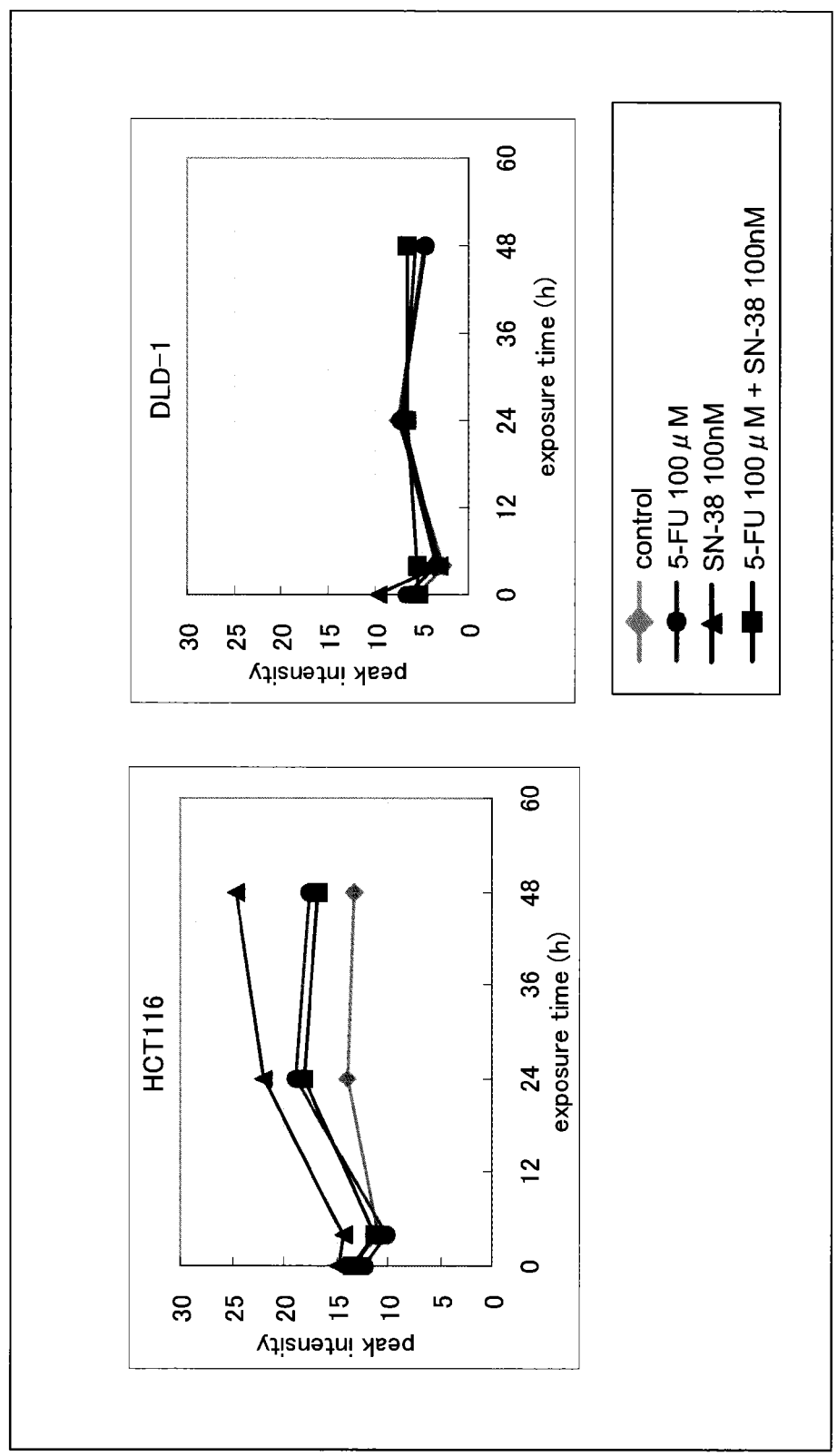
FIG. 2 A graph showing a time-dependent profile of the intracellular protein A level in HCT116 cells after exposure to 5-FU, SN-38, or 5-FU/SN-38, and a graph showing the time-dependent profile of the intracellular protein A level in DLD-1 cells after exposure to 5-FU, SN-38, or 5-FU/SN-38.
Figure 3:
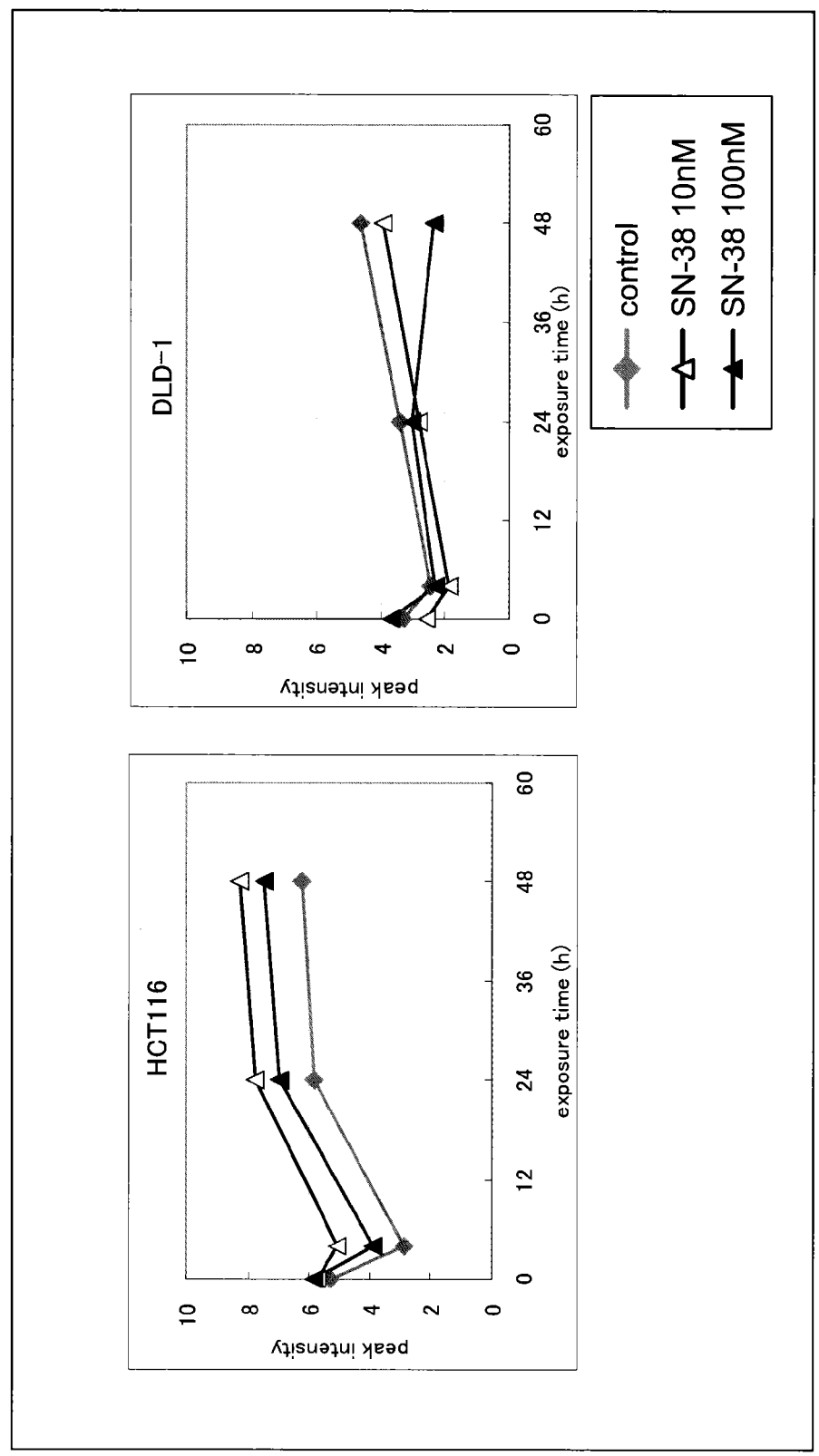
FIG. 3 A graph showing a time-dependent profile of the intracellular protein B level in HCT116 cells after exposure to SN-38, and a graph showing the time-dependent profile of the intracellular protein B level in DLD-1 cells after exposure to SN-38.
Figure 4:
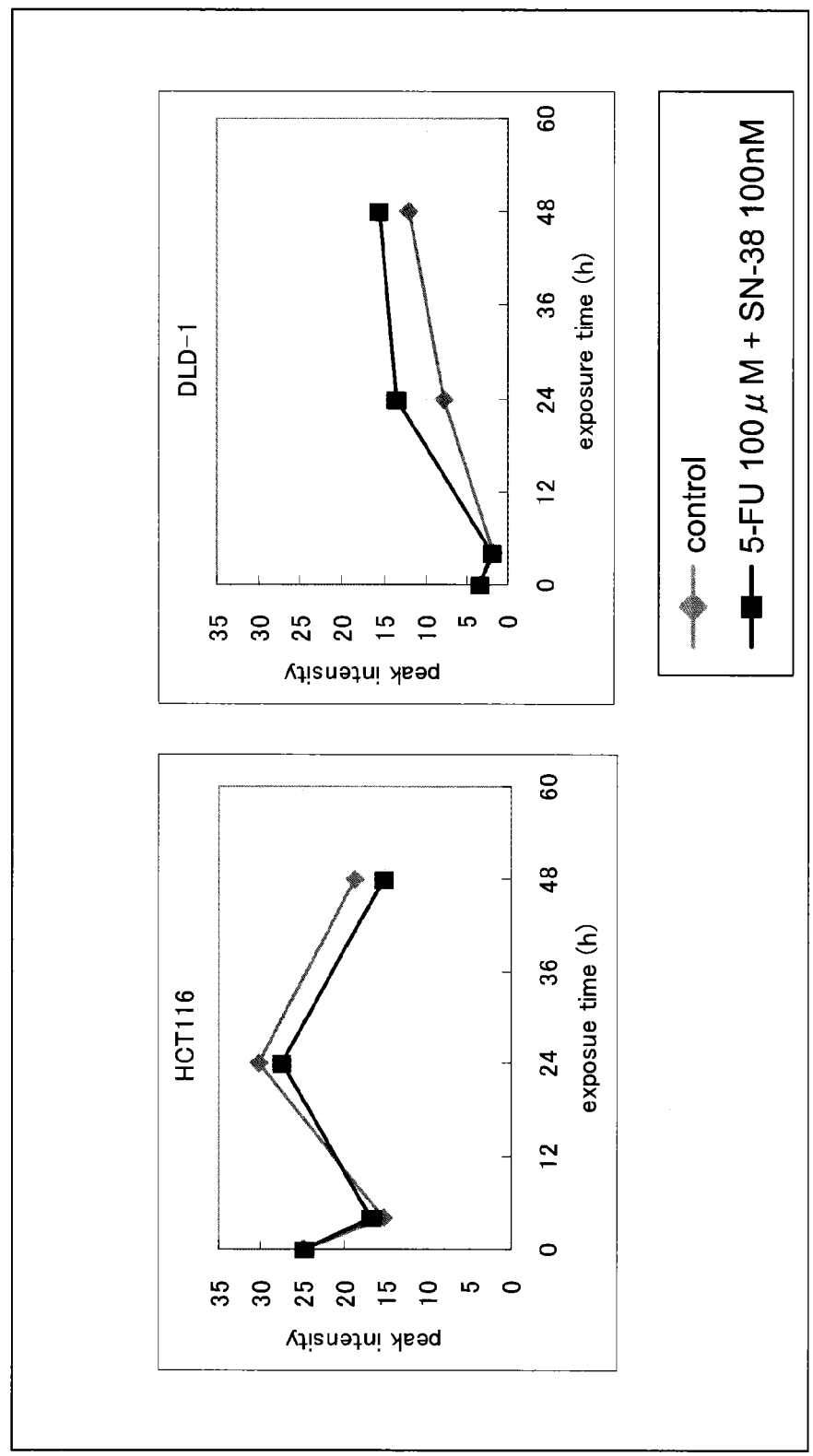
FIG. 4 A graph showing a time-dependent profile of the intracellular protein C level in HCT116 cells after exposure to 5-FU/SN-38, and a graph showing the time-dependent profile of the intracellular protein C level in DLD-1 cells after exposure to 5-FU/SN-38.

(1) Peaks exhibiting, after exposure to 5-FU, a protein level increase in HCT116 (FIG. 2)
m/z of 16,450 to 16,620 (protein A)
(2) Peaks exhibiting, after exposure to SN-38, a protein level increase in HCT116 (FIGS. 2 and 3)
m/z of 16,450 to 16,620 (protein A)
m/z of 22,080 to 22,310 (protein B)
(3) Peaks exhibiting, after exposure to 5-FU/SN-38 combination, a protein level increase in HCT116 (FIG. 2)
m/z of 16,450 to 16,620 (protein A)
(4) Peaks exhibiting, after exposure to 5-FU/SN-38 combination, a protein level increase in DLD-1 (FIG. 4)
m/z of 17,100 to 17,270 (protein C)
(5) Peaks exhibiting, before drug exposure (not exposed), a protein level significantly higher in HCT116 than in DLD-1
m/z of 16,450 to 16,620 (protein A)
m/z of 22,080 to 22,310 (protein B)
m/z of 17,100 to 17,270 (protein C)

Intracellular protein A levels before drug exposure, represented by a peak intensity obtained by SELDI-TOF MS analysis (µA) (av. ±S.D., n=27), were 15.0±3.30 (HCT116) and 8.59±3.49 (DLD-1). Similarly, intracellular protein B levels were 5.95±1.10 (HCT116) and 2.99±0.81 (DLD-1), and protein C levels were 26.9±3.94 (HCT116) and 5.01±2.01 (DLD-1). Thus, these proteins exhibited an intracellular level significantly higher in HCT116 than in DLD-1, before drug exposure (not exposed).

Example 2

All the peaks (m/z) detected in Example 1 (an m/z of 16,450 to 16,620 (protein A or fragment thereof), an m/z of 22,080 to 22,310 (protein B or fragment thereof), and an m/z of 17,100 to 17,270 (protein C or fragment thereof)) were confirmed through internal molecular weight calibration by use of two molecular weight standards sandwiching a target peak. The following standard substances having a known molecular weight were employed: cytochrome c (equine) (m/z: 12360.96+1 H), apomyoglobin (equine) (m/z: 16952.27+1 H), and aldorase (rabbit muscle) (m/z: 39212.28+1 H). As a result, proteins A, B, and C detected in Example 1 were found to be detected at an m/z of 16,450 to 16,620, an m/z of 22,080 to 22,310, and an m/z of 17,100 to 17,270, respectively.

Example 3

The features of the peaks found in Example 1 (an m/z of 16,450 to 16,620 (protein A or fragment thereof), an m/z of 22,080 to 22,310 (protein B or fragment thereof), and an m/z of 17,100 to 17,270 (protein C or fragment thereof)) were further investigated in terms of variation in peak intensity associated with change in pH.

(1) Method (a) ProteinChip Array and Buffer Conditions Employed in the Study

For a cation-exchange ProteinChip array (CM10, Bio-Rad), the following 15 types of buffers were used: pH: 3.0 (50 mM glycine-HCl buffer), pH: 3.5 (50 mM sodium acetate buffer), pH: 4.0 (50 mM sodium acetate buffer), pH: 4.5 (50 mM sodium acetate buffer), pH: 5.0 (50 mM sodium acetate buffer), pH: 5.5 (50 mM sodium acetate buffer), pH: 6.0 (50 mM phosphate buffer), pH: 6.5 (50 mM phosphate buffer), pH: 7.0 (50 mM phosphate buffer), pH: 7.5 (50 mM phosphate buffer), pH: 8.0 (50 mM Tris-HCl buffer), pH: 8.5 (50 mM Tris-HCl buffer), pH: 9.0 (50 mM glycine-NaOH buffer), pH: 9.5 (50 mM glycine-NaOH buffer), and pH: 10.0 (50 mM glycine-NaOH buffer).

(b) Preparation of Samples for CM10 Chip Array Analysis and Analysis Conditions

Preparation of samples for CM10 chip array analysis, and production of protein chips were performed by use of buffers of (a) in accordance with (f) of method (1) of Example 1.

(2) Results

In the CM10 chip array analysis, the pH at which the relevant peak intensity drops is thought to be the isoelectric point (pI) of the protein, where an ionized form is neutralized. As a result, the peaks detected in Example 1 were found to have the following estimated isoelectric points (pIs):

a pH of 4.5 to 7.5 (m/z of 16,450 to 16,620 (protein A)),
a pH of 4.0 to 7.0 (m/z of 22,080 to 22,310 (protein B)), and,
a pH of 5.0 to 8.0 (m/z of 17,100 to 17,270 (protein C)).

Example 4

Based on the results of Examples 2 and 3, the peaks detected in Example 1 (an m/z of 16,450 to 16,620 (protein A or fragment thereof), an m/z of 22,080 to 22,310 (protein B or fragment thereof), and an m/z of 17,100 to 17,270 (protein C or fragment thereof)) were subjected to database searching by use of TagIdent tool (http://au.expasy.org/tools/tagident.html) of The ExPASy proteomics server. The results are as follows.

TABLE 1

| Proteins or fragments thereof detected | Results of retrieval Protein name (UniProtKB/Swiss-Prot Accession number) |
|---|---|
| Protein A | Protein S100-A1-like. (A6NMZ2), PTPN13-like protein, Y-linked. (O14603), Microsomal glutathione S-transferase 3. (O14880), Coagulation factor IXa light chain. (P00740), Myosin light chain 3, skeletal muscle isoform. (P06741), Caspase-3 subunit p17. (P42574), Cyclin-dependent kinase inhibitor 2A, isoforms 1/2/3. (P42771), Presenilin-2 CTF subunit (By similarity). (P49810), Ubiquitin-conjugating enzyme E2 D1. (P51668), Voltage-dependent calcium channel subunit alpha-2/delta-1 (P54289), Glia maturation factor beta. (P60983), Regenerating islet-derived protein 3 alpha. (Q06141), Leukotriene C4 synthase. (Q16873), Uncharacterized protein C11orf36. (Q2M3A8), Coiled-coil domain-containing protein 58. (Q4VC31), Putative uncharacterized protein C9orf122. (Q5SY85), Protein FAM72A. (Q5TYM5), Putative uncharacterized protein C10orf113. (Q5VZT2), Regenerating islet-derived protein 3 gamma. (Q6UW15), Transmembrane protein C17orf87. (Q6UWF3), Spermatogenesis-associated protein 19, mitochondrial. (Q7Z5L4), Protein FAM72B. (Q86X60), Uncharacterized protein FLJ37310. (Q8N1X5), AN1-type zinc finger protein 2A. (Q8N6M9), LIM domain only protein 3. (Q8TAP4), Uncharacterized protein C22orf15. (Q8WYQ4), Thyroid hormone-inducible hepatic protein. (Q92748), Uncharacterized protein C20orf173. (Q96LM9), Dual specificity protein phosphatase 23. (Q9BVJ7), Keratin-associated protein 9-4. (Q9BYQ2), Group II F secretory phospholipase A2. (Q9BZM2), Uncharacterized protein C14orf56. (Q9H7N3), Protein EMI5 homolog, mitochondrial. (Q9NX18), Protein phosphatase 1 regulatory subunit 14D. (Q9NXH3), Voltage-dependent calcium channel subunit alpha-2/delta-2. (Q9NY47), Putative protein FAM30A. (Q9NZY2), NADH dehydrogenase |

TABLE 1-continued

| Proteins or fragments thereof detected | Results of retrieval Protein name (UniProtKB/Swiss-Prot Accession number) |
|---|---|
| | [ubiquinone] 1 alpha subcomplex subunit 13. (Q9P0J0), Psoriasis susceptibility 1 candidate gene 1 protein. (Q9UIG5) |

TABLE 2

| Proteins or fragments thereof detected | Results of retrieval Protein name (UniProtKB/Swiss-Prot Accession number) |
|---|---|
| Protein B | Uncharacterized protein C2orf74. (A8MZ97), Tumor protein D54. (O43399), Density-regulated protein. (O43583), Carcinoembryonic antigen-related cell adhesion molecule 4. (O75871), Somatotropin. (P01241), Chorionic somatomammotropin hormone. (P01243), Superoxide dismutase [Mn], mitochondrial. (P04179), Beta-crystallin A3, isoform A1, Delta8 form. (P05813), UMP-CMP kinase. (P30085), Hippocalcin-like protein 1. (P37235), Chromobox protein homolog 5. (P45973), Beta-crystallin A4. (P53673), Ubiquitin-conjugating enzyme E2 K. (P61086), Neurocalcin-delta. (P61601), Neuron-specific calcium-binding protein hippocalcin. (P84074), Dr1-associated corepressor. (Q14919), Mediator of RNA polymerase II transcription subunit 22. (Q15528), Coiled-coil domain-containing protein 85B. (Q15834), Transcription elongation factor A protein-like 6. (Q6IPX3), Charged multivesicular body protein 1b. (Q7LBR1), Transmembrane protein 61. (Q8N0U2), Fin bud initiation factor homolog. (Q8TAL6), Protein FAM3C. (Q92520), Loss of heterozygosity 12 chromosomal region 1 protein. (Q969J3), Transmembrane 4 L6 family member 18. (Q96CE8), Ubiquitin-conjugating enzyme E2 E2. (Q96LR5), B-cell CLL/lymphoma 7 protein family member B. (Q9BQE9), Twisted gastrulation protein homolog 1. (Q9GZX9), Ras-related protein Rab-1B. (Q9H0U4), Variable charge X-linked protein 1. (Q9H320), Membrane-spanning 4-domains subfamily A member 5. (Q9H3V2), DnaJ homolog subfamily C member 5. (Q9H3Z4), Sodium channel subunit beta-3. (Q9NY72), Securin-2. (Q9NZH5), COMM domain-containing protein 3. (Q9UBI1), Transmembrane emp24 domain-containing protein 3. (Q9Y3Q3) |

TABLE 3

| Proteins or fragments thereof detected | Results of retrieval Protein name (UniProtKB/Swiss-Prot Accession number) |
|---|---|
| Protein C | Oocyte-expressed protein homolog. (A6NGQ2), Putative calcium-activated potassium channel subunit beta-3-like protein. (A8MYL6), Heat shock protein beta-6. (O14558), HERV-K_5q33.3 provirus ancestral Pro protein. (P10265), Nucleoside diphosphate kinase A. (P15531), Stathmin. (P16949), Interleukin-1 receptor antagonist protein. (P18510), 3-hydroxyanthranilate 3,4-dioxygenase. (P46952-2), Glycoprotein Xg. (P55808), Caveolin-3. (P56539), Ubiquitin- |

TABLE 3-continued

| Proteins or fragments thereof detected | Results of retrieval Protein name (UniProtKB/Swiss-Prot Accession number) |
|---|---|
| | conjugating enzyme E2 N. (P61088), Protein mago nashi homolog. (P61326), HERV-K_12q14.1 provirus ancestral Pro protein. (P63119), HERV-K_19q12 provirus ancestral Pro protein. (P63120), HERV-K_19p13.11 provirus ancestral Pro protein. (P63121), HERV-K_1q23.3 provirus ancestral Pro protein. (P63123), HERV-K_5q13.3 provirus ancestral Pro protein. (P63124), HERV-K_22q11.21 provirus ancestral Pro protein. (P63129), Microfibrillar-associated protein 5. (Q13361), Protein CROC-4. (Q13536), Protein CROC-4. (Q13536), Frataxin (56-210). (Q16595), Protein FAM182A. (Q5T1J6), Putative uncharacterized protein FLJ42147. (Q6ZVS6), Uncharacterized protein C14orf65. (Q8N9R9), Protein mago nashi homolog 2. (Q96A72), Uncharacterized protein UNQ773/PRO1567. (Q96DA0), FXYD domain-containing ion transport regulator 5. (Q96DB9), Transcription factor BTF3 homolog 4. (Q96K17), Lipopolysaccharide-induced tumor necrosis factor-alpha factor. (Q99732), Complexin-3. (Q8WVH0), Nucleoside diphosphate kinase, mitochondrial. (O00746), Tumor necrosis factor ligand superfamily member 12. (O43508), Cytochrome c oxidase subunit 4 isoform 1, mitochondrial. (P13073), HERV-K_8p23.1 provirus ancestral Pro protein. (P63122), HERV-K_6q14.1 provirus ancestral Pro protein. (P63127), Putative RNA-binding protein 3. (P98179), Putative RRN3-like protein FLJ77916. (Q2M238), Protein ZNF767. (Q75MW2), FUN14 domain-containing protein 1. (Q8IVP5), Putative uncharacterized protein C20orf78. (Q9BR46), Transmembrane protein C9orf46. (Q9HBL7), H/ACA ribonucleoprotein complex subunit 2. (Q9NX24), Chemokine-like factor. (Q9UBR5), RING finger protein 24. (Q9Y225), Uncharacterized protein C5orf50. (A6NLE4), ATP synthase subunit d, mitochondrial. (O75947), HERV-K_1p13.3 provirus ancestral Gag polyprotein. (P62686), Troponin C, slow skeletal and cardiac muscles. (P63316), UPF0484 protein FAM167B. (Q9BTA0), Protein FAM176B. (Q9NVM1), Uncharacterized protein LOC389203. (Q8N5G0), Putative uncharacterized protein C12orf33. (Q8N6U2) |

The invention claimed is:

1. A method for treating colorectal cancer in a subject in need thereof which comprises
   (a) obtaining a biological sample from a subject having colorectal cancer;
   (b) determining the absence or presence of at least one marker selected from the group consisting of a protein or a fragment thereof which is detected as a peak at m/z of 16,450 to 16,620, a protein or a fragment thereof which is detected as a peak at m/z of 22,080 to 22,310, and a protein or a fragment thereof which is detected as a peak at m/z of 17,100 to 17,270, in said biological sample obtained in (a) by mass spectrometry and then for each peak detected indicating the presence of said at least one marker determining the concentration of the marker corresponding to the peak detected;
   (c) administering to said subject a anticancer agent selected from the group consisting of fluorouracil, SN-38, and irinotecan, or a salt thereof;
   (d) obtaining a biological sample from said subject following said administering;
   (e) determining the absence or presence of at least one marker selected from the group consisting of a protein or a fragment thereof which is detected as a peak at m/z of 16,450 to 16,620, a protein or a fragment thereof which is detected as a peak at m/z of 22,080 to 22,310, and a protein or a fragment thereof which is detected as a peak at m/z of 17,100 to 17,270, in said biological sample obtained in (d) by mass spectrometry and then for each peak detected indicating the presence of said at least one marker determining the concentration of the marker corresponding to the peak detected;
   (f) comparing the concentration of said at least one marker measured in (e) to the concentration of said at least one marker measured in (b) to determine whether said colorectal cancer is sensitive to said anticancer agent, wherein:
   sensitivity is determined by measuring a concentration of protein A having a peak at m/z of 16,450 to 16,620 wherein when the concentration of protein A in (e) is greater than the concentration of protein A in (b) said subject is determined to have sensitivity to the anti-cancer agent,
   sensitivity is determined by measuring a concentration of protein B having a peak at m/z of 22,080 to 22,310 wherein when the concentration of protein B in (e) is greater than the concentration of protein B in (b) said subject is determined to have sensitivity to the anti-cancer agent, and/or
   sensitivity is determined by measuring a concentration of protein C having a peak at m/z of 17,100 to 17,270 wherein when the concentration of protein C in (e) is the same as or less than the concentration of protein C in (b) said subject is determined to have sensitivity to the anti-cancer agent
   (g) continuing administration of said anti-cancer agent where said colorectal cancer is determined to be sensitive to said anti-cancer agent or discontinuing administration of said anti-cancer agent where said colorectal cancer is determined to not be sensitive to said anti-cancer agent,
   wherein the concentration determination is by assessing mass spectrometry peak intensities of said markers.

2. The method according to claim 1, wherein the biological sample is blood.

3. The method according to claim 1, wherein the biological sample is serum.

4. The method according to claim 1, wherein the anti-cancer agent is fluorouracil or a salt thereof.

5. The method according to claim 1, wherein the anti-cancer agent is a combination of fluorouracil or a salt thereof with irinotecan, SN-38, or a salt thereof.

6. The method according to claim 1, wherein the biological sample is plasma.

7. The method according to claim 1, wherein the biological sample is a cancer tissue biopsy specimen.

8. The method according to claim 1, wherein the biological sample is a cancer isolated preparation.

9. The determination method according to claim 1, wherein the biological sample is feces.

10. The method according to claim 1, wherein the biological sample is urine.

11. The method according to claim 1, wherein the biological sample is ascitic fluid.

12. The method according to claim 1, wherein the biological sample is pleural fluid.

13. The method according to claim 1, wherein the biological sample is cerebrospinal fluid.

14. The method according to claim 1, wherein the biological sample is expectoration.

15. The method according to claim 1, wherein the anti-cancer agent is irinotecan or a salt thereof.

16. The method according to claim 1, wherein the anti-cancer agent is SN-38 or a salt thereof.

17. The method according to claim 1, wherein sensitivity is determined by measuring a concentration of protein A having a peak at m/z of 16,450 to 16,620 wherein when the concentration of protein A in (e) is greater than the concentration of protein A in (b) said subject is determined to have sensitivity to the anti-cancer agent.

18. The method according to claim 1, wherein sensitivity is determined by measuring a concentration of protein B having a peak at m/z of 22,080 to 22,310 wherein when the concentration of protein B in (e) is greater than the concentration of protein B in (b) said subject is determined to have sensitivity to the anti-cancer agent.

19. The method according to claim 1, wherein sensitivity is determined by measuring a concentration of protein C having a peak at m/z of 17,100 to 17,270 wherein when the concentration of protein C in (e) is the same as or less than the concentration of protein C in (b) said subject is determined to have sensitivity to the anti-cancer agent.

20. The method according to claim 1, wherein said mass spectrometer is a surface-enhanced laser desorption/ionization time-of-flight mass spectrometer.

21. The method according to claim 1, further comprising extracting intracellular proteins from the obtained biological sample prior to said determining.

22. The method according to claim 1, wherein the extracted intracellular proteins are subjected to ProteinChip array analysis.

* * * * *